United States Patent [19]

Matsuoka et al.

[11] Patent Number: 4,510,264
[45] Date of Patent: Apr. 9, 1985

[54] PROCESS FOR THE PREPARATION OF A CATALYST FOR THE SYNTHESIS OF METHANE

[75] Inventors: Hiroo Matsuoka; Seiichi Matsuoka; Tsunekichi Yamabe; Hirokazu Fujie; Kenji Mori; Kouji Tamura; Masatoshi Yamada; Akio Furuta, all of Handa, Japan

[73] Assignee: JGC Corporation, Otemachi, Japan

[21] Appl. No.: 528,107

[22] Filed: Aug. 31, 1983

[30] Foreign Application Priority Data

Oct. 1, 1982 [JP] Japan .................................. 57-173085
Mar. 16, 1983 [JP] Japan .................................. 58-42235
Apr. 22, 1983 [JP] Japan .................................. 58-70085

[51] Int. Cl.$^3$ ............................................. B01J 23/74
[52] U.S. Cl. ..................................... 502/328; 518/717
[58] Field of Search ...................... 502/328, 330, 335; 518/717

[56] References Cited

U.S. PATENT DOCUMENTS 3,119,667 1/1964 McMahon ...................... 502/330 X
3,320,182 5/1967 Taylor et al. ........................ 502/328
4,151,190 4/1979 Murchison et al. ............ 502/330 X

FOREIGN PATENT DOCUMENTS 1055909 1/1967 United Kingdom ................ 518/717

Primary Examiner—W. J. Shine
Attorney, Agent, or Firm—Bucknam and Archer

[57] ABSTRACT

A catalyst for the synthesis of methane by the hydrogenation of carbon monoxide and/or carbon dioxide, comprising alumina, nickel and barium or sodium; and a process for the preparation of said catalyst, comprising firstly having barium or sodium carried on alumina and secondly having nickel carried thereon.

1 Claim, 5 Drawing Figures

FIG. 1

BaO Content (Wt.%)

PROCESS FOR THE PREPARATION OF A CATALYST FOR THE SYNTHESIS OF METHANE

This invention relates to a catalyst for use in the synthesis of methane by the hydrogenation of carbon oxide and also to a process for the preparation of the catalyst. More particularly, it relates to a catalyst, which comprises alumina, nickel and barium or sodium, for use in the synthesis of methane from a gas containing carbon oxide in a high concentration and also to a process for the preparation of the catalyst. The term "carbon oxide" used herein is intended to mean carbon monoxide and/or carbon dioxide.

A process for methanating a carbon oxide-rich gas obtained by the gasification of a heavy fraction oil or coal thereby to produce a substitute natural gas, is a very promising one from the view-point of the recent situation of energy. There have recently been published many reports on the methane synthesis from gases obtained by the gasification of coal. A full-scale study of such synthesis has been made particularly in U.S.A. and, on the other hand, a project to produce high calorific gases has been established as a part of Sunshine Project in Japan. The proposed catalysts for producing methane from carbon oxide, include, for example, Ni-Mo-MgO, Ni-Mo-$ZrO_2$ and Ni-Fe-$MgAl_2O_4$.

The methanation or methane synthesis reaction is one accompanied with the production of a lot of reaction heat and it is very important from the view-point of economy of a methane synthesis process to effectively utilize said reaction heat as an energy source. To this end, it is the most preferable to cause the reaction to take place at high temperatures; however, it is known that the use of a catalyst, which is usually employed in the methane synthesis reaction, in such a carbon oxide-rich gas atmosphere will result in causing sintering and producing carbonaceous material and the like due to the heat production and presence of steam in the atmosphere, whereby the catalyst is remarkably degraded.

Further, the carbonaceous material produced on the catalyst by carbon atoms combining together, sometimes cause the plugging of reaction tubes thereby rendering it physically impossible to continue the reaction.

Many processes which have hitherto been proposed in order to solve such problems contemplate to keep the temperature control of the catalyst layer by always removing the reaction heat to avoid a high-temperature reaction. However, these processes lose the advantage that the reaction heat is recovered for its effective utility.

An object of this invention is to provide a methane synthesizing catalyst which will not catalytically degrade even at high temperatures so that such reaction heat may be recovered for its effective utility.

Another object is to provide a process for the preparation of such a catalyst.

These and other objects of this invention may be achieved by the use of the following catalyst.

The catalyst of this invention is a methane-producing catalyst comprising alumina, nickel and barium or sodium.

In a case where the catalyst comprises alumina, nickel and barium, the amount of nickel used in the catalyst is in the range of preferably 0.05–30%, by weight of a total of the nickel and alumina, and the amount of barium contained in the catalyst is in the range of preferably 0.3–9.0% by weight as oxide of the alumina that is 0.27–8.06% by weight as barium. The use of less than 0.05% by weight of nickel will not exhibit its effect, while the use of xore than 30% by weight of nickel will generate locally too much heat. The higher nickel content the catalyst has, the higher catalytic activity and the greater heat evolution it exhibits. Thus, in a case where higher catalytic activity catalytic activity is desired with no significant problem due to great heat evolution, the nickel content of 3–30 wt. %, economically preferably 5–15 wt. %, is desired; on the other hand, in a case where mild catalytic activity is desired without raising a problem as to great heat evolution, the nickel content of 0.05 to less than 3 wt. % is desired. The nickel content in this range will result in inhibiting local heat generation and preventing the degradation of the catalyst thereby exhibiting practically excellent catalytic activity as a methanation catalyst.

More particularly, if a usual nickel-type methanation catalyst is used in a process such as the present process, there will be raised problems as to the degradation of activity of the catalyst and the heat removal of an apparatus used because of great heat evolution due to too high initial catalytic activity. To overcome these troubles, it is necessary to take procedures such as the use of diluted catalyst and a decrease in the amount of raw gas supplied. However, such procedures raise technical and economical problems. To this end, it has been thought to decrease the nickel content in the resulting catalyst although conventional catalysts contain 2–3% to 20–30% of nickel; however, a decrease in content of nickel beyond a certain level will incur a remarkable decrease in initial activity thereby decreasing the catalytic activity. The use of less than 0.3% by weight of barium as oxide based on the weight of alumina will not exhibit its effect, while the use of more than 9.0% by weight of barium as oxide will make it difficult to carry the oxide on a carrier by means of the usual impregnation method because of low solubility of barium nitrate and barium hydroxide; thus the barium is necessarily carried on the carrier by means of a blending technique prior to molding a material for the carrier, however, the barium so blended will not exhibit great effects for its large amount. Therefore, the use of more than 9 wt. % of barium as oxide is not so meritorious The barium containing catalyst of this invention may be manufactured by contacting an alumina carrier with a solution of a barium salt such as barium nitrate, barium hydroxide or barium carbonate and a solution of a nickel salt such as nickel nitrate, by means of a conventional known technique such as an impregnation, blending or precipitation. In this manufacture, the following three methods (1) to (3) may be used:

(1) a method comprising adding a barium salt solution to an alumina carrier, pyrolyzing the barium salt to obtain a barium-containing alumina carrier which is then incorporated with a nickel salt solution;

(2) a method comprising mixing two such solutions together and then having the resulting mixture carried on an alumina carrier; and (3) a method comprising having NiO carried on an alumina carrier and then having BaO carried on the NiO-carried alumina carrier.

Among these three methods, the method (1) is particularly desired.

In a case where the catalyst comprises alumina, nickel and sodium, the amount of nickel in the catalyst is in the range of economically preferably 0.05–30%, more preferably 2–30%, by weight of the alumina.

The amount of sodium is preferably such that the ratio in number between the sodium atoms and the nickel atoms is in the range of from 0.02 to 0.6. In other words, the amount of sodium is in the range of from 0.106 to 3.169 wt. % calculated as sodium oxide when the content of nickel is 10 wt. %. The use of less than said lower limit (0.106 wt. %) of sodium will exhibit little effects that sodium inhibits carbon deposition, while the use of more than said upper limit (0.6 wt. %) thereof will disadvantageously result in decreasing the methanation activity of the catalyst since the pores of the alumina carrier are plugged with the sodium thereby decreasing the surface area of the alumina carrier and the nickel atoms are covered with an excess of the sodium thereby decreasing the active surface area of the nickel.

One reason for preventing carbon deposition by the presence of sodium in the catalyst, would be that the surface is chemically changed thereby to inhibit the formation of active sites which will cause carbon deposition.

The sodium-containing catalyst of this invention may be obtained by contacting an alumina carrier with not only a solution of a sodium salt such as sodium nitrate but also a solution of a nickel salt such as nickel nitrate by a conventional known technique such as an impregnation, blending or precipitation whereby the nickel and sodium are carried on the alumina carrier.

In this case, there may be used the following three methods (1) to (3):

(1) a method comprising carrying sodium on an alumina carrier and then adding nickel to the sodium-carried alumina carrier;

(2) a method comprising carrying nickel and sodium on an alumina carrier at the same time; and (3) a method comprising carrying nickel on an alumina carrier and then carrying sodium on the nickel-carried alumina carrier, with the method (1) being preferred from the view-point of catalytic activity.

It is the most preferred that the alumina used in this invention be γ-alumina.

This invention will be better understood by the following examples, comparative examples and experiments by reference to the accompanying drawings.

COMPARATIVE EXAMPLE 1

One hundred (100) grams of molded alumina carrier (γ-alumina; water absorbing capacity, 0.75 c.c./g) were placed in a 500-c.c. beaker and impregnated with 75 c.c. of a nickel nitrate solution (2.53 mol/l, pH 1.7) while shaking up the alumina carrier, and adding said solution dropwise at a room temperature. Thereafter, the alumina carrier so impregnated was allowed to stand still for 12 hours at room temperature for achieving uniform impregnation, dried in a dryer and then baked at 500° C. in air for 3 hours in an electric furnace in the conventional manner thereby to obtain a catalyst No. 1 having a nickel content of 10 wt. %.

EXAMPLE 1

One hundred (100) g of the same alumina carrier as used in Comparative Example 1 were placed in a 500-c.c. beaker and impregnated with 75 c.c. of a barium nitrate solution (0.26 mol/l) while adding said solution dropwise to the carrier at room temperature. The thus impregnated alumina carrier was allowed to stand still for 12 hours, thereafter dried in a usual manner and then baked at 800° C. in air for 3 hours in an electric furnace to carry 3 wt. % (based on the weight of alumina) of barium as oxide on the alumina carrier.

The thus barium-carried alumina carrier was impregnated with 75 c.c. of a nickel nitrate solution (2.53 mol/l) while adding the solution dropwise to the carrier, allowed to stand still for 12 hours, dried in a usual manner and then baked at 500° C. in air for 3 hours in an electric furnace thereby to obtain a catalyst No. 2.

EXAMPLES 2-4

The procedure of Example 1 was followed, but varying the concentration of a barium nitrate solution, thereby to obtain two barium-containing alumina carriers respectively having barium contents of 0.6 wt. % and 1.5 wt. % as oxide. In addition, the procedure of Example 1 was also followed except that 150 c.c. of a barium nitrate solution (0.39 mol/l) were added in two portions to the alumina carrier material to impregnate it with the solution thereby to obtain a barium-containing alumina carrier having a barium content of 9 wt. % as oxide.

One hundred grams of each of these three barium-carried alumina carriers (barium contents of 0.6, 1.5 and 9 wt. % as oxide, respectively) were treated in the same manner as in Example 1 to carry NiO thereon thereby obtaining catalysts Nos. 3, 4 and 5.

EXAMPLE 5

The same catalyst No. 1 as obtained in Comparative Example 1 was placed in a 500-c.c. beaker and impregnated with 75 c.c. of a barium nitrate solution (0.26 mol/l) while adding the solution dropwise to the catalyst No. 1 at room temperature. The catalyst No. 1 so impregnated was allowed to stand still at room temperature for 12 hours, dried in a usual manner and then baked at 500° C. in air for 3 hours in an electric furnace to obtain a catalyst No. 6 containing barium in an amount of 3 wt. % as oxide of the alumina.

EXAMPLE 6

The same alumina carrier having 9 wt. % barium as oxide carried thereon as obtained in Example 4 was impregnated with 289 c.c. of a nickel nitrate solution (2.53 mol/l) in three portions and then treated in the same manner as in Example 4 thereby to obtain a catalyst No. 7 having a nickel content of 30 wt. %.

EXPERIMENT 1

The same catalysts Nos. 1 to 5 as obtained in Comparative Example 1 and Examples 1-4, respectively, were each measured for their remaining surface area ratio from sintering in a steam atmosphere using a usual flow-type fixed bed reactor.

The measurement was effected as follows.

Two (2) grams of each of the catalysts were filled in a stainless steel-made 16-mm inner diameter reaction tube of the reactor, treated with 50 l/hr of $H_2$ and 80 c.c./hr of $H_2O$ (molar ratio of $H_2O/H_2$ being 2) passing at 600° C. and 10 Kg/cm$^2$.G through the reaction tube over a time period of 24 hours and then measured for remaining surface area ratio S/So (So: pre-treatment surface area; S: surface area after treatment). The thus-measured remaining surface area ratio for each catalyst is as shown in FIG. 1.

Figure 1:
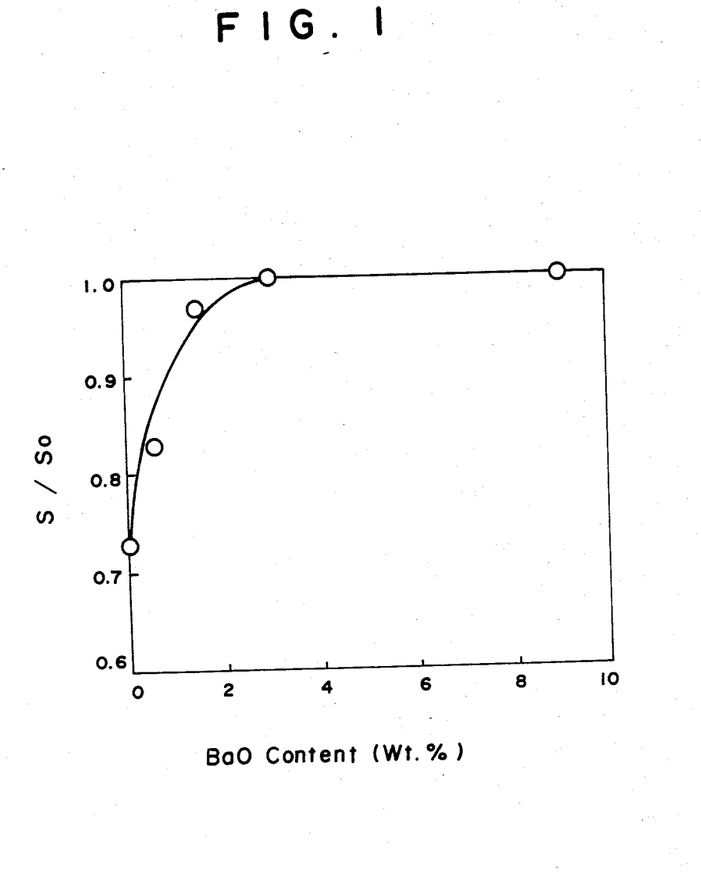
FIG. 1 is a graph showing the relationship between the remaining surface area ratio (S/So) and barium content as oxide (wt. %) in Experiment 1.

It is seen from FIG. 1 that the BaO contained in the catalyst was effective in resistance to sintering of the catalyst.

EXPERIMENT 2

The same catalysts Nos. 1, 2 and 6 as obtained in Comparative Example 1 and Examples 1 and 5, respectively, were each tested for variation in methanating activity without addition of steam.

Using a usual high-pressure flow-type fixed bed reactor wherein 0.2 g of each catalyst is filled in the stainless steel-made reaction tube, the reaction was effected by passing 60 l/hr of $H_2$ and 20 l/hr of CO at 350° C. (at the entrance of the reaction tube) and 10 Kg/cm$^2$.G and at a GHSV of 270,000 hr$^{-1}$ through the reactor over a time period of 100 hours, to measure the CO conversion rate. The results are as shown in FIG. 2.

Figure 2:
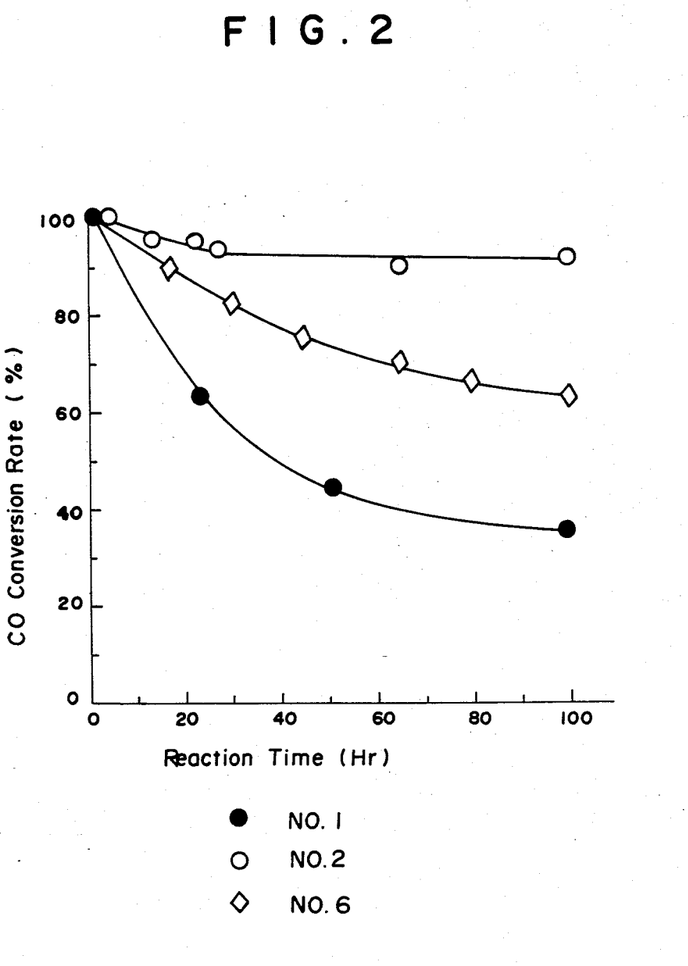
FIG. 2 is a graph showing the relationship between the CO conversion rate (%) and reaction time (hr) in Experiment 2.

It is seen from FIG. 2 that the presence of BaO in the catalysts remarkably lessened the degradation of the catalysts.

Table 1 shows the properties of the catalysts 1, 2 and 6 before and after the use thereof. As is seen from Table 1, the presence of barium in the catalysts inhibited carbon deposition effectively.

TABLE 1

| Catalyst No. | Remaining surface area ratio (S/So) | Amount of carbon deposited (wt. %) |
| --- | --- | --- |
| 1 | 0.96 | 1.30 |
| 2 | 0.98 | 0.48 |
| 6 | 0.98 | 0.82 |
| 7 | 0.97 | 0.49 |

EXPERIMENT 3

The same catalysts 1 and 2 respectively as obtained in Comparative Example 1 and Example 1 were measured for variation in methanating activity in the presence of steam. The reactor used was the same as used in Experiment 2 and the reaction was effected as follows.

0.2 g of each catalyst were filled in the stainless steel-made reaction tube having a 16-mm inner diameter in said reactor, after which 60 l/hr of $H_2$, 20 l/hr of CO and 32.1 g/hr of $H_2O$ (molar ratio: $H_2O/CO=2$) were passed at 350° C. (at the entrance of the reaction tube) and 10 Kg/cm$^2$.G through the reaction tube at a GHSV of 270,000 hr$^{-1}$ (without $H_2O$), to measure the CO conversion rate. The conversion rate so measured was 100% for each of the catalysts Nos. 1 and 2. Thereafter, the conversion was effected at a gas temperature of 600° C. (at the entrance of the reaction tube) for 100 hours and it was then effected again at 350° C. (at the entrance of the reaction tube) to measure the conversion rate.

The effect of the BaO contained in the catalyst No. 2 in comparison with the catalyst No. 1 was estimated by the CO conversion rate, remaining surface area ratio and amount of carbon deposited, each obtained by the above experiment comprising treating, in the presence of each of the catalysts, the gases at 600° C. and then at 350° C. as mentioned above. The results are as shown in Table 2.

TABLE 2

| Catalyst No. | CO conversion rate (%) | Remaining surface area ratio (S/So) | Amount of carbon deposited (wt. %) |
| --- | --- | --- | --- |
| 1 | 37.4 | 0.72 | 0.26 |
| 2 | 74.0 | 0.86 | 0.27 |

It is seen from Table 2 that the barium contained in catalyst No. 2 inhibited the sintering thereof under the conditions at high temperatures and prevented the degradation of activity of the catalyst.

As previously mentioned, a process for the production of a high calorific gas comprising methanating a CO-rich gas obtained by the gasification of a heavy fraction oil or coal, is considered to be very promising; however, there has never been developed a suitable catalyst which may be used in such a promising process as mentioned above. The catalysts comprising alumina, nickel, barium or sodium according to this invention will sparingly degrade even when used in such a promising process and are advantageous particularly in their heat resistance at high temperatures and pressures in a steam atmosphere as well as in their inhibition of carbon deposition. Thus, they allow the reaction to be effected at high temperatures whereby the heat produced may be recovered as high-temperature steam and the energy efficiency may consequently be increased.

COMPARATIVE EXAMPLE 2

One hundred (100) grams of the same molded alumina carrier (water absorbing capacity: 0.75 c.c./g) were placed in a 500-c.c. beaker and impregnated with 75 c.c. of a nickel nitrate solution (0.68 mol/l) while shaking up the carrier material and adding the solution dropwise thereto at room temperature. The thus impregnated alumina carrier was allowed to stand still at room temperature for 12 hours to ensure uniform impregnation, dried in a drier in a usual manner and then baked at 500° C. in air for 3 hours in an electric furnace thereby to obtain a catalyst No. 8 having a 2.9 wt. % nickel content.

COMPARATIVE EXAMPLES 3–5

The procedure of Comparative Example 2 was followed except that each of nickel nitrate solutions having different concentrations was used, thereby to obtain catalysts Nos. 9–11 having nickel contents of 5.0 wt. %, 2.0 wt. % and 0.5 wt. %, respectively.

EXAMPLES 7 and 7'

One hundred (100) grams of the same alumina carrier as used in Comparative Example 2 were placed in a 500-c.c. beaker and impregnated with 75 c.c. of a barium nitrate solution (0.26 mol/l) while shaking up the alumina carrier and adding the solution dropwise thereto at room temperature. The alumina carrier so impregnated was allowed to stand still at room temperature for 12 hours to ensure uniform impregnation, dried in a drier in a usual manner and then baked at 800° C. for 3 hours in a muffle furnace to obtain an alumina carrier which carried thereon barium in an amount of 3.0 wt. % as oxide of the alumina.

The barium-carried alumina carrier was impregnated with 75 c.c. of a nickel nitrate solution (0.68 mol/l) while adding the solution dropwise in the same manner as in Comparative Example 2. The carrier so impregnated was allowed to stand still for 12 hours, dried in a usual manner and then baked at 500° C. in air for 3 hours in an electric furnace thereby to obtain a catalyst No. 12 having a 2.9 wt. % nickel content and a 3.0 wt. % barium as oxide content. Following the procedure of Example 7, but varying the concentration of nickel nitrate solution, there was obtained a catalyst No. 13 having a 3 wt. % barium as oxide content and a 5 wt. % nickel content.

COMPARATIVE EXAMPLE 6 AND EXAMPLES 8-10

The same alumina carrier having 3.0 wt. % of barium as oxide carried thereon as obtained in Example 7, was impregnated with each of solutions having different nickel nitrate concentrations in the same manner as in Example 7 thereby to obtain catalysts Nos. 14 to 17 having nickel contents of 2.0 wt. %, 0.5 wt. %, 0.05 wt. % and 0.03 wt. %, respectively.

EXAMPLE 11

The same catalyst No. 8 having a 2.9 wt. % nickel content as prepared in Comparative Example 2 was placed in a 500-c.c. beaker and impregnated with 75 c.c. of a barium nitrate solution (0.26 mol/l) while adding the solution dropwise to the catalyst. The catalyst so impregnated was allowed to stand still at room temperature for 12 hours, dried in a usual manner and then baked at 500° C. in air for 3 hours in an electric furnace thereby to obtain a catalyst No. 18 on which 3.0 wt. %, based on the alumina, of barium as oxide was carried.

The nickel content (based on the total of nickel and alumina) and barium as oxide content (based on alumina) of the catalysts Nos. 8-18 so far obtained, are as shown in Table 3.

EXAMPLE 12

Following the procedure of Example 7, but varying the concentration of each of a barium nitrate solution and nickel nitrate solution, there was obtained a catalyst No. 19 having an 0.3 wt. % barium as oxide content and an 0.05 wt. % nickel content.

EXPERIMENT 4

The catalysts Nos. 8-18 obtained in Comparative Examples 2-7 and Examples 7-11 were measured for their initial methanating reaction velocity (ro) by the use of a usual atmospheric-pressure flow-type fixed bed reactor under the following reaction conditions.

The catalysts were each crushed to obtain catalyst particles having particle sizes of 10 to 16 mesh. The catalysts so crushed were each used in an amount of 0.1 to 10 g depending on their catalytic activity. The reaction tube used was a Pyrex brand glass tube having a 20-mm inner diameter. The crushed catalysts were each diluted with an alumina carrier, packed in the reaction tube, reduced at 500° C. for one hour in a hydrogen stream and then contacted with 9 l/hr of $H_2$ and 3 l/hr of CO (molar ratio of $H_2$/CO: 3) at 290° C. and atmospheric pressure to measure the initial methanating activity. The catalyst layer was provided with a 3-mm thermowell to measure the temperature thereof. In this experiment, the CO conversion rates obtained by the catalysts were all 10% or less so as to keep substantially isothermal condition in the catalyst layer. The initial methanating reaction velocities (ro) so measured are as shown in Table 3 and FIG. 3.

Figure 3:
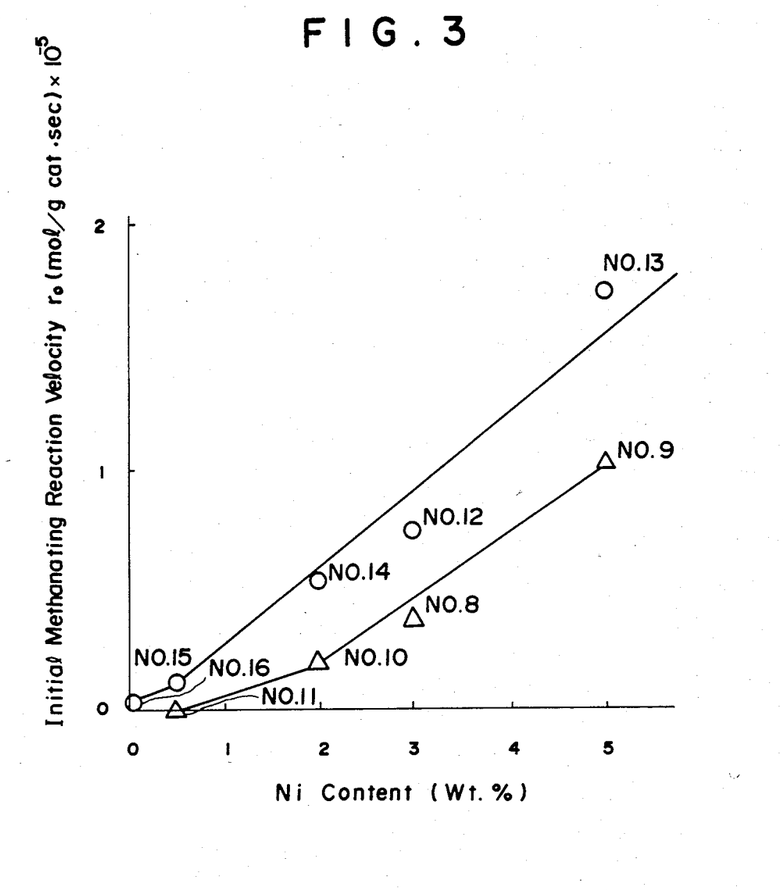
FIG. 3 is a graph showing the relationship between the initial methanating reaction velocity (r) and nickel content of each of catalysts 8-16 in Experiment 4.

It is seen from these Table and Figure that the barium oxide present in the catalyst increases the initial methanating activity thereof and allows the catalyst to exhibit comparatively desirable activity even if the catalyst contains nickel in an amount of as small as 0.5% by weight. On the other hand, in a case where the catalyst does not contain barium oxide, it hardly exhibits activity when it contains nickel in an amount of only 0.5% by weight. It is seen from the above that barium oxide present in such a catalyst is effective in increasing the initial methanating activity of the catalyst. The catalyst No. 18 of Example 11 obtained by having barium oxide carried subsequent to having nickel carried is inferior in initial methanating activity to the catalyst No. 12 of Example 7 obtained by having barium oxide carried prior to having nickel carried.

EXPERIMENT 5

The same catalysts Nos. 8-18 as obtained in Comparative Examples 2-7 and Examples 7-11 respectively, were tested at high temperatures in a steam atmosphere for variation in methanating activity by the use of a usual high-pressure through type fixed layer reactor. This experiment was made as follows.

The catalysts were each filled in a stainless steel-made reaction tube having a 16-mm inner diameter and contacted with 50 l/hr of $H_2$ and 80 c.c./hr of $H_2O$ (molar ratio of $H_2/H_2O$: 2) at 600° C. and 10 Kg/cm².G for 24 hours. The final methanating reaction velocity (r) for each catalyst at the end of the 24 hours' experiment was as indicated in Table 3. In addition, the ratios (r/ro) of said reaction velocities (r) to those (ro) obtained in Experiment 4 are as shown in Table 3 and FIG. 4 to investigate the variation in activity.

TABLE 3

| Example and Comparative Example | Catalyst No. | Nickel content (wt. %) | Barium as oxide content (wt. %) | Initial methanating reaction velocity (ro) (mol/g-Cat · sec) | Final methanating reaction velocity (r) (mol/g-Cat · sec) | r/r0 (—) |
| --- | --- | --- | --- | --- | --- | --- |
| Comp. Ex. 2 | 8 | 2.9 | 0 | $3.6 \times 10^{-6}$ | $6.6 \times 10^{-7}$ | 0.18 |
| Comp. Ex. 3 | 9 | 5.0 | 0 | $1.0 \times 10^{-5}$ | $3.7 \times 10^{-6}$ | 0.37 |
| Comp. Ex. 4 | 10 | 2.0 | 0 | $1.8 \times 10^{-6}$ | 0.0 | 0.0 |
| Comp. Ex. 5 | 11 | 0.5 | 0 | 0.0 | 0.0 | 0.0 |
| Example 7 | 12 | 2.9 | 3.0 | $7.2 \times 10^{-6}$ | $3.0 \times 10^{-6}$ | 0.42 |
| Example 7' | 13 | 5.0 | 3.0 | $1.7 \times 10^{-5}$ | $7.9 \times 10^{-6}$ | 0.46 |
| Example 8 | 14 | 2.0 | 3.0 | $5.2 \times 10^{-6}$ | $2.0 \times 10^{-6}$ | 0.38 |
| Example 9 | 15 | 0.5 | 3.0 | $1.1 \times 10^{-6}$ | $2.2 \times 10^{-7}$ | 0.20 |
| Example 10 | 16 | 0.05 | 3.0 | $6.0 \times 10^{-8}$ | $5.4 \times 10^{-9}$ | 0.09 |

TABLE 3-continued

| Example and Comparative Example | Catalyst No. | Nickel content (wt. %) | Barium as oxide content (wt. %) | Initial methanating reaction velocity (ro) (mol/g-Cat · sec) | Final methanating reaction velocity (r) (mol/g-Cat · sec) | r/r0 (—) |
|---|---|---|---|---|---|---|
| Comp. Ex. 6 | 17 | 0.03 | 3.0 | 0.0 | 0.0 | 0.0 |
| Example 11 | 18 | 2.9 | 3.0 | $3.3 \times 10^{-6}$ | $1.0 \times 10^{-6}$ | 0.30 |
| Example 12 | 19 | 0.05 | 0.3 | $3.2 \times 10^{-8}$ | $2.5 \times 10^{-9}$ | 0.08 |

Note:
Comp. Ex. = Comparative Example

Figure 4:
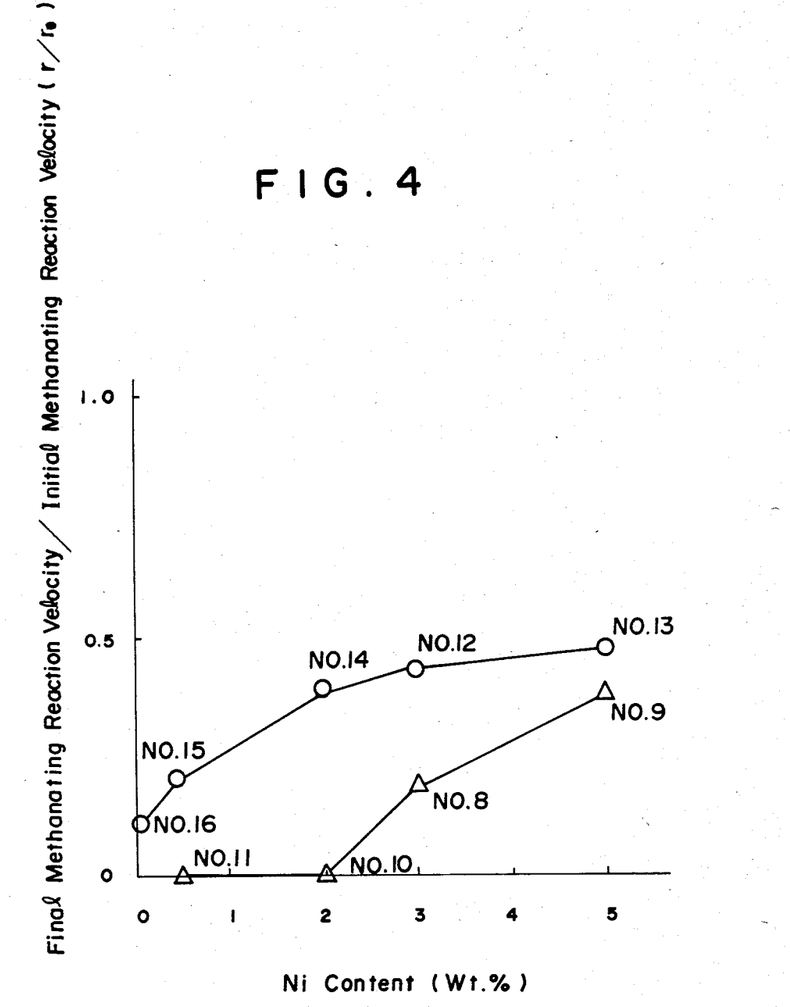
FIG. 4 is a graph showing the relationship between the ratio (r/ro) of the final methanating reaction velocity (r) to the initial one (ro) and the nickel content of each of the catalysts Nos. 8-16.

As is clear from Table 3 and FIG. 4, the catalysts Nos. 8–11 containing no barium oxide will remarkably decrease in final methanating reaction velocity after a high-temperature treatment in a steam atmosphere. This is remarkably true particularly with the catalysts Nos. 10 and 11 having a low nickel content. In contrast, the catalysts Nos. 12–16 containing barium oxide will exhibit a still high methanating reaction velocity after the same treatment, this proving that they are excellent in keeping methanating actiyity stably. The ratio of r/ro of the catalysts Nos. 12–16 is higher as the nickel content thereof is higher, however, even the catalysts Nos. 14–16 having a low nickel content will exhibit desired methanating activity although the catalysts Nos. 10–11 containing no barium oxide will exhibit a remarkable decrease in catalytic activity during their use.

COMPARATIVE EXAMPLES 7-8

One hundred (100) grams of the same alumina carrier as used in Comparative Example 1 were placed in a 500-c.c. beaker and then treated in the same manner as in Comparative Example 1 except that the concentration of nickel nitrate solution used was varied, thereby to obtain catalysts Nos. 20 and 21 respectively having nickel contents of 2 wt. % and 6 wt. %.

COMPARATIVE EXAMPLES 9-10

One hundred (100) grams of the same alumina carrier as used in Comparative Example 1 were introduced into a 500-c.c. beaker and impregnated with 150 c.c. of a nickel nitrate solution (2.53 mol/l) in two portions to obtain catalysts No. 22 having a 20 wt. % nickel content. One of the thus obtained catalysts was further impregnated with 225 c.c. of a nickel nitrate solution (2.53 mol/l) in three portions to obtain a catalyst No. 23 having a 30 wt. % nickel content.

EXAMPLE 13

One hundred (100) grams of the same alumina carrier as used in Comparative Example 1 were introduced into a 500-c.c. beaker, impregnated with 75 c.c. of a sodium nitrate solution (0.26 mol/l) while shaking up the carrier and adding the solution dropwise thereto at room temperature, dried in a drier in a usual manner and then baked at 800° C. for 3 hours in a muffle furnace to have sodium carried on the alumina carrier. The sodium-carried alumina carrier was impregnated with 75 c.c. of a nickel nitrate solution (2.53 mol/l) while adding the solution dropwise thereto, thereafter allowed to stand still for 12 hours, dried in a usual manner and then baked at 500° C. in air for 3 hours in an electric furnace thereby to obtain a catalyst No. 24 having 0.6 wt. % sodium oxide content and a 10 wt. % nickel content.

EXAMPLES 14-17

Following the procedure of Example 13, but varying the concentration of sodium nitrate solution used, there were obtained alumina carriers respectively having sodium oxide contents of 0.2 wt. %, 0.4 wt. %, 1.2 wt. % and 2.4 wt. %. The sodium oxide-carried alumina carriers so obtained were each impregnated with 75 c.c. of a nickel nitrate solution (2.53 mol/l) while adding the solution dropwise in the same manner as in Example 13, thereafter dried in a usual manner and then baked at 500° C. in air for 3 hours in an electric furnace thereby to obtain catalysts Nos. 25, 26, 27 and 28 having a 10 wt. % nickel content each.

EXAMPLE 18

One hundred (100) grams of the same alumina carrier as used in Comparative Example 1 were placed in a 500-c.c. beaker, impregnated with 75 c.c. of a sodium nitrate solution (0.052 mol/l) while adding the solution dropwise to the carrier at room temperature, thereafter dried in a usual manner and then baked at 800° C. for 3 hours in a muffle furnace thereby to obtain an alumina carrier having an 0.12 wt. % sodium as oxide content. The sodium-carried alumina carrier so obtained was impregnated with 75 c.c. of a nickel nitrate solution (0.506 mol/l) while adding the solution dropwise to the carrier, allowed to stand still for 12 hours, dried in a usual manner and then baked at 500° C. in air for 3 hours in an electric furnace thereby to obtain a catalyst No. 29 having a 2 wt. % nickel content.

EXAMPLE 19

One hundred (100) grams of the same alumina carrier as used in Comparative Example 1 were placed in a 500-c.c. beaker, impregnated with 75 c.c. of a sodium nitrate solution (0.78 mol/l) while adding the solution dropwise to the carrier at room temperature, thereafter dried in a usual manner and then baked at 800° C. for 3 hours in a muffle furnace to carry 1.8 wt. % of sodium as oxide on the alumina carrier. The sodium-carried alumina carrier was impregnated with 225 c.c. of a nickel nitrate solution (2.53 mol/l) in three portions thereby to obtain a catalyst No. 30 having a 30 wt. % nickel content.

EXAMPLE 20

The same catalyst No. 1 (127.25 g) as prepared in Comparative Example 1 was introduced into a 500-c.c. beaker, impregnated with 75 c.c. of a sodium nitrate solution (0.26 mol/l) while adding the solution dropwise to the catalyst at room temperature, allowed to stand still at room temperature for 12 hours, dried in a usual manner and then baked at 500° C. in air for 3 hours in an electric furnace thereby to obtain a catalyst No. 31 having an 0.6 wt. % sodium as oxide content.

COMPARATIVE EXAMPLE 11

One hundred (100) grams of the same alumina carrier as used in Comparative Example 1 was introduced into a 500-c.c. beaker, impregnated with 75 c.c. of a potassium nitrate solution (0.26 mol/l) while adding it dropwise to the carrier at room temperature, thereafter dried in a usual manner and then baked at 800° C. for 3 hours in a muffle furnace to have 0.9 wt. % of potassium as oxide carried on the alumina carrier. This potassium-carried alumina carrier was impregnated with 75 c.c. of a nickel nitrate solution while adding it dropwise to the carrier, allowed to stand still for 12 hours, dried in a usual manner and then baked at 500° C. in air for 3 hours in an electric furnace thereby to obtain a catalyst No. 32 having a 10 wt. % nickel content.

EXPERIMENT 6

The catalysts Nos. 1, 20–23, 24, 29 and 30 obtained respectively in Comparative Examples 1 and 8–11 and Examples 12, 17 and 18, were measured for their initial methanating activity under differential reaction conditions by the use of a usual atmospheric-pressure flow-type fixed bed reactor. The reaction was effected by passing 9 l/hr of $H_2$ and 3 l/hr of CO at a reaction temperature of 290° C. through a Pyrex brand glass reaction tube (inner diameter: 14 mm) packed with 0.05–0.3 g of each of the catalysts to find the methanating activity thereof. The results are as indicated in Table 4.

TABLE 4

| Catalyst No. | Methanating reaction velocity (mol/g-cat · sec) |
|---|---|
| 1 | $2.5 \times 10^{-5}$ |
| 20 | $2.0 \times 10^{-6}$ |
| 21 | $1.2 \times 10^{-5}$ |
| 22 | $4.5 \times 10^{-5}$ |
| 23 | $5.7 \times 10^{-5}$ |
| 24 | $2.3 \times 10^{-5}$ |
| 29 | $2.1 \times 10^{-6}$ |
| 30 | $5.5 \times 10^{-5}$ |

As is apparent from Table 4, the catalysts Nos. 1 and 20–23 vary in initial methanating activity with a change of nickel content, while the catalysts Nos. 24, 29 and 30 are approximately the same in initial methanating activity as the catalysts Nos. 1, 20 and 23 which have the same Ni contents as the former, respectively. This indicates that the sodium present in the catalyst will not decrease the methanating activity thereof.

EXPERIMENT 7

The catalysts Nos. 1 and 24–27 obtained respectively in Comparative Example 1 and Examples 12–15, were tested for variation in methanating activity without the addition of steam.

Using a usual high-pressure through-type fixed-layer reactor, the methanating reaction was effected by passing 60 l/hr of $H_2$ and 20 l/hr of CO at a GHSV of 270,000 $hr^{-1}$ through the stainless steel-made reaction tube (inner diameter: 16 mm) of said reactor, packed with 0.2 g of each of the catalysts, the reaction being continued at a pressure of 10 $Kg/cm^2$.G and a gas temperature of 350° C. at the entrance of the reaction tube for 100 hours, thereby to measure CO conversion rate. The results are as shown in FIG. 5.

Figure 5:
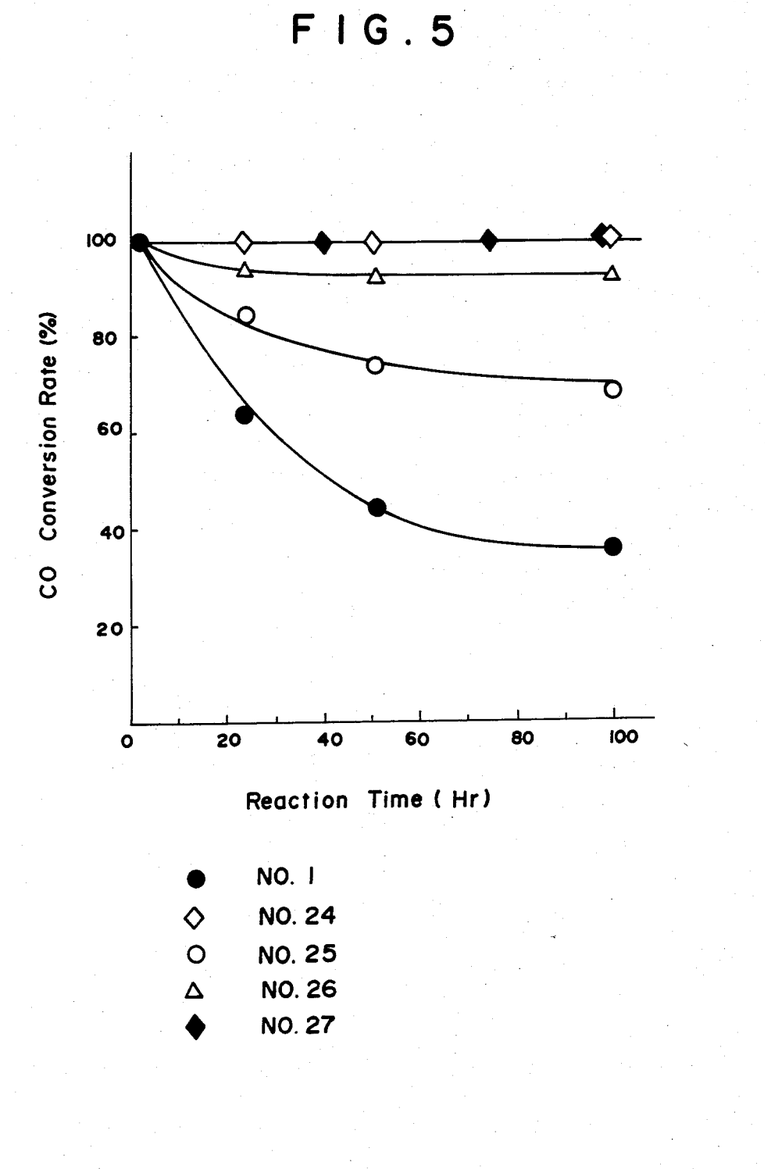
FIG. 5 is a graph showing the relationship between the CO conversion rate (%) and reaction time (hr) in Experiment 7.

It is seen from FIG. 5 that the catalysts Nos. 24–27 containing sodium will remarkably decrease in catalytic degradation with the lapse of time as compared with the catalyst No. 1.

EXPERIMENT 8

The catalysts Nos. 1 and 23–32 respectively obtained in Comparative Examples 1, 10 and 11 and Examples 12–19 were tested for the amount of carbon deposited thereon after the end of methanating reaction without the addition of steam to the reaction system. With respect to the reaction, the procedure (including the use of a reaction tube packed with 0.2 g of each of the catalysts, passage of raw gases at 10 $Kg/cm^2$.G and 350° C. through the reaction tube for 100 hours, etc.) of Experiment 7 was followed. The amount of carbon deposited on each of the catalysts after the end of the reaction is as shown in Table 5.

TABLE 5

| Catalyst No. | Ni content (wt. %/$Al_2O_3$) | Sodium as oxide content (wt. %/$Al_2O_3$) | Na/Ni (atomic ratio) | Amount of carbon (wt. %) | Amount of carbon (g-Carbon/g-Ni) | Remarks |
|---|---|---|---|---|---|---|
| 1 | 10 | 0 | 0 | 1.30 | 0.13 | |
| 20 | 2 | 0 | 0 | — | — | Catalyst No. 31 Ni impregnated after impregnation of Ni |
| 21 | 6 | 0 | 0 | — | — | |
| 22 | 20 | 0 | 0 | — | — | |
| 23 | 30 | 0 | 0 | 4.52 | 0.15 | Catalyst No. 32 $K_2O$ carried |
| 24 | 10 | 0.6 | 0.114 | 0.16 | 0.016 | |
| 25 | 10 | 0.2 | 0.038 | 0.56 | 0.056 | |
| 26 | 10 | 0.4 | 0.076 | 0.30 | 0.03 | |
| 27 | 10 | 1.2 | 0.227 | 0.16 | 0.016 | |
| 28 | 10 | 2.4 | 0.454 | 0.16 | 0.016 | |
| 29 | 2 | 0.12 | 0.114 | 0.03 | 0.015 | |
| 30 | 30 | 1.8 | 0.114 | 0.73 | 0.024 | |
| 31 | 10 | 0.6 | 0.114 | 0.56 | 0.056 | |
| 32 | 10 | 0.9 ($K_2O$) | 0.112 (K/Ni) | 13.2 | 1.32 | |

Table 5 indicates the amount of carbon deposited on each of the catalysts Nos. 1 and 23–32 as well as the nickel content, sodium oxide content (potassium oxide content) and atomic ratio of Na (or K)/Ni of each of the catalysts Nos. 1 and 20–32. The sodium-containing catalysts Nos. 24–31 greatly decreased in amount of carbon deposited thereon as compared with the sodium-free catalyst No. 1. The catalyst No. 24 obtained by having sodium carried prior to having nickel carried is seen to have allowed carbon to deposit thereon in a small amount as compared with the catalyst No. 31 obtained by having nickel carried prior to having sodium carried. The catalyst No. 32 containing potassium which is one of the alkali metals as sodium is, is not desirable because of a remarkably large amount of carbon deposited thereon.

As previously mentioned, a process for the methanation of a CO-rich gas obtained by the gasification of a heavy fraction oil or coal is a very promising process, however, there have heretofore not been obtained a suitable catalyst which may be used under severe reaction conditions in said promising process. The catalysts of this invention comprising alumina, nickel and barium oxide or sodium may be conveniently used as a catalyst for the synthesis of methane since they will be very effective in inhibiting carbon precipitation which is a serious factor of catalyst degradation and will not appreciably decrease in methanating activity during their use in the methanation of CO-containing gases.

It should be noted that in cases where the barium nitrate solution was added to alumina carrier in Example 4 or the nickel nitrate solution was added in two or three portions to the alumina carrier in Examples 6 and 18 as well as in Comparative Examples 9 and 10, the subsequent treatment (including drying and baking at 800° C. for the impregnated barium nitrate solution or at 500° C. for the impregnated nickel nitrate solution) was effected every impregnation with the portion of the solution.

What is claimed is:

1. A process for preparing a catalyst for the synthesis of methane by the hydrogenation of carbon monoxide and/or carbon dioxide, comprising adding a barium salt solution to alumina, pyrolyzing the barium salt to obtain barium oxide carried on alumina and then adding a nickel salt solution to said barium oxide carried on alumina, pyrolyzing the nickel salt to obtain nickel oxide carried thereon, the amount of barium oxide so carried being in the range of 0.27–8.06 wt. % of the alumina as barium, the amount of nickel oxide so carried being in the range of 0.05–30 wt. % as nickel of the total of the alumina and nickel.

* * * * *